United States Patent
Otaki et al.

(10) Patent No.: US 10,386,308 B2
(45) Date of Patent: Aug. 20, 2019

(54) PATTERN INSPECTION APPARATUS FOR DETECTING A PATTERN DEFECT

(71) Applicant: Nuflare Technology, Inc., Yokohama-shi (JP)

(72) Inventors: Toshiaki Otaki, Yokohama (JP); Riki Ogawa, Kawasaki (JP)

(73) Assignee: NuFlare Technology, Inc., Yokohama-shi (JP)

( * ) Notice: Subject to any disclaimer, the term of this patent is extended or adjusted under 35 U.S.C. 154(b) by 91 days.

(21) Appl. No.: 15/642,905

(22) Filed: Jul. 6, 2017

(65) Prior Publication Data

US 2018/0024075 A1    Jan. 25, 2018

(30) Foreign Application Priority Data

Jul. 19, 2016   (JP) ................. 2016-141737

(51) Int. Cl.
| | |
|---|---|
| *G01N 21/88* | (2006.01) |
| *G01N 21/956* | (2006.01) |
| *G06T 7/00* | (2017.01) |

(52) U.S. Cl.
CPC ....... *G01N 21/8806* (2013.01); *G01N 21/956* (2013.01); *G06T 7/0004* (2013.01); *G01N 2021/8848* (2013.01)

(58) Field of Classification Search
None
See application file for complete search history.

(56) References Cited

U.S. PATENT DOCUMENTS

| | | | |
|---|---|---|---|
| 8,203,706 B2 | 6/2012 | Shibata et al. | |
| 9,804,103 B2 | 10/2017 | Tsuchiya et al. | |
| 2008/0123506 A1* | 5/2008 | Morimoto | ............. G03H 1/16 |
| | | | 369/103 |
| 2009/0279079 A1 | 11/2009 | Shibata et al. | |

(Continued)

FOREIGN PATENT DOCUMENTS

| | | |
|---|---|---|
| JP | 5352111 B2 | 11/2013 |
| JP | 2014-157142 | 8/2014 |
| KR | 10-2015-0130919 A | 11/2015 |

OTHER PUBLICATIONS

Office Action dated May 30, 2018 in Korean Patent Application No. 10-2017-0085455 with English translation, citing documents AO and AP therein, 8 pages.

*Primary Examiner* — Edemio Navas, Jr.
(74) *Attorney, Agent, or Firm* — Oblon, McClelland, Maier & Neustadt, L.L.P.

(57) ABSTRACT

A pattern inspection apparatus includes a first half-wave plate to receive an ultraviolet light linearly polarized in a first electric field oscillation direction, and output a linearly polarized light polarized in a second electric field oscillation direction obtained by rotating by an integer multiple of 90°, a mirror to reflect the linearly polarized light polarized in the second electric field oscillation direction, and output a linearly polarized light polarized in a third electric field oscillation direction parallel or orthogonal to the second electric field oscillation direction, a second half-wave plate to convert the linearly polarized light polarized in the third electric field oscillation direction, which has been reflected, to a linearly polarized light polarized in a fourth electric field oscillation direction by rotating by an angle different from an integer multiple of 90°.

10 Claims, 7 Drawing Sheets

(56) References Cited

U.S. PATENT DOCUMENTS

2014/0232849 A1\* 8/2014 Ogawa .................. G06T 7/0004
  348/87
2015/0332452 A1 11/2015 Tsuchiya et al.

\* cited by examiner

PATTERN INSPECTION APPARATUS FOR DETECTING A PATTERN DEFECT

CROSS-REFERENCE TO RELATED APPLICATION

This application is based upon and claims the benefit of priority from the prior Japanese Patent Application No. 2016-141737 filed on Jul. 19, 2016 in Japan, the entire contents of which are incorporated herein by reference.

BACKGROUND OF THE INVENTION

Field of the Invention

Embodiments of the present invention relate generally to a pattern inspection apparatus, and, for example, to an inspection apparatus for inspecting defects of a pattern, whose size is smaller than the resolution limit of an inspection light, formed on a template used for nanoimprint technology.

Description of Related Art

In recent years, nanoimprint lithography (NIL) has attracted attention as a technology for forming micropatterns. According to this technology, by pressing a mold (die) having a nanoscale microstructure onto a resist on a semiconductor wafer, micropatterns are formed on the resist. In the nanoimprint technology, a plurality of duplicate templates (replica templates) are created using a master template as the original, and, each replica template is placed on a different nanoimprint apparatus to be used. The replica template needs to be produced to accurately correspond to the master template. Therefore, not to mention the master template, high accuracy is required when a pattern on the replica template is evaluated.

Regarding an exposure apparatus typified by a stepper apparatus which exposes/transfers a pattern onto a resist film on a wafer, a pattern formed on the exposure mask substrate is reduced to, for example, one-fourth to be exposed/transferred. By contrast, in the nanoimprint technology, since a pattern formed on the template is exposed/transferred without magnification or reduction, the formed pattern size itself is originally small. Conventionally, in an inspection apparatus, the shape of a pattern is specified by irradiating a pattern forming surface with an ultraviolet light as an inspection light. However, with recent miniaturization, since the size of a pattern formed on the template is less than the wavelength of a light used for the inspection apparatus, and smaller than the resolution limit, it becomes difficult to directly specify the pattern shape.

Patterns formed on the template are in many cases repetitive patterns having a periodic regularity, such as typified by line and space patterns. If there is a defect in such a repetitive pattern with a periodic regularity, disturbance (disorder) of the periodicity occurs. When the defective portion at which the periodicity is disturbed is image-captured, disturbance occurs in a polarization state of light of the pattern image. Therefore, it is now examined to inspect a pattern defect by detecting an image-captured position where disturbance occurs in the polarization state (e.g., refer to Japanese Unexamined Patent Publication No. 2014-157142).

Regarding the polarization state, if a repetitive pattern is irradiated with, for example, a light with a polarization direction parallel to the longitudinal direction of a line pattern of the repetitive pattern, disturbance does not occur or is unlikely to occur in the polarization state of light of an acquired pattern image. Therefore, the polarization angle of the illumination light should be adjusted so as not to be in the same direction as the longitudinal direction of the line pattern. Regarding an illumination optical system, a mirror is generally used in the optical path of the system. When an illumination light such as described above is reflected by the mirror, disturbance often occurs in the polarization state of the reflected illumination light. Therefore, even if a repetitive pattern, being smaller than the resolution limit and having a periodic regularity, is irradiated with the illumination light in which the polarization state disturbance has occurred, it is difficult to determine whether the disturbance of the polarization state of light of an acquired pattern image is caused by the mirror or by a pattern defect.

BRIEF SUMMARY OF THE INVENTION

According to one aspect of the present invention, a pattern inspection apparatus includes a first half-wave plate configured to receive an ultraviolet light linearly polarized in a first electric field oscillation direction, and output a linearly polarized light polarized in a second electric field oscillation direction obtained by rotating the first electric field oscillation direction of the ultraviolet light by an integer multiple of 90°, a mirror configured to reflect the linearly polarized light polarized in the second electric field oscillation direction, and output a linearly polarized light polarized in a third electric field oscillation direction parallel or orthogonal to the second electric field oscillation direction, a second half-wave plate configured to convert the linearly polarized light polarized in the third electric field oscillation direction, which has been reflected, to a linearly polarized light polarized in a fourth electric field oscillation direction by rotating the linearly polarized light polarized in the third electric field oscillation direction by an angle different from an integer multiple of 90° so as to output the linearly polarized light polarized in the fourth electric field oscillation direction, a stage configured to mount thereon a substrate, on which a repetitive pattern having a size smaller than a resolution limit of the ultraviolet light is formed, such that the repetitive pattern is repeated in a direction parallel or orthogonal to the third electric field oscillation direction, an objective lens configured to make the linearly polarized light rotated in the fourth electric field oscillation direction by the second half-wave plate illuminate the repetitive pattern formed on the substrate, and a sensor configured to receive a transmitted light of the repetitive pattern smaller than the resolution limit or a reflected light from the repetitive pattern smaller than the resolution limit, which has been irradiated with the linearly polarized light polarized in the fourth electric field oscillation direction obtained by rotating the third electric field oscillation direction by the angle different from the integer multiple of 90° by the second half-wave plate.

According to another aspect of the present invention, a pattern inspection method includes reflecting by a mirror an ultraviolet light linearly polarized which is controlled to be in an electric field oscillation direction where an electric field oscillation direction of an incident light into the mirror and an electric field oscillation direction of a reflected light from the mirror are parallel to each other in a case of reflecting by the mirror the ultraviolet light linearly polarized; controlling the electric field oscillation direction of the reflected light to be an angle different from an integer multiple of 90° relative to a periodic direction of a repetitive pattern formed on a substrate repeating by a size smaller than a resolution limit of the ultraviolet light; irradiating the substrate with the reflected light having been controlled to be the angle different from the integer multiple of 90° relative to the periodic direction of the repetitive pattern; receiving a pattern image of the repetitive pattern, reflected from the substrate, by a sensor through the mirror; and inspecting the pattern image received by the sensor.

According to yet another aspect of the present invention, a pattern inspection method includes reflecting by a mirror an ultraviolet light linearly polarized which is controlled to be in an electric field oscillation direction where an electric field oscillation direction of an incident light into the mirror and a travel direction of a reflected light from the mirror are parallel to each other in a case of reflecting by the mirror the ultraviolet light linearly polarized; controlling the electric field oscillation direction of the reflected light to be an angle different from an integer multiple of 90° relative to a periodic direction of a repetitive pattern formed on a substrate repeating by a size smaller than a resolution limit of the ultraviolet light; irradiating the substrate with the reflected light having been controlled to be the angle different from the integer multiple of 90° relative to the periodic direction of the repetitive pattern; receiving a pattern image of the repetitive pattern, reflected from the substrate, by a sensor through the mirror; and inspecting the pattern image received by the sensor.

DETAILED DESCRIPTION OF THE INVENTION

First Embodiment

A first embodiment of the present invention describes an inspection apparatus which can detect a pattern defect even when a repetitive pattern, being smaller than the resolution limit and having a periodic regularity, is irradiated using an illumination optical system where a mirror is arranged on an optical path.

Figure 1:
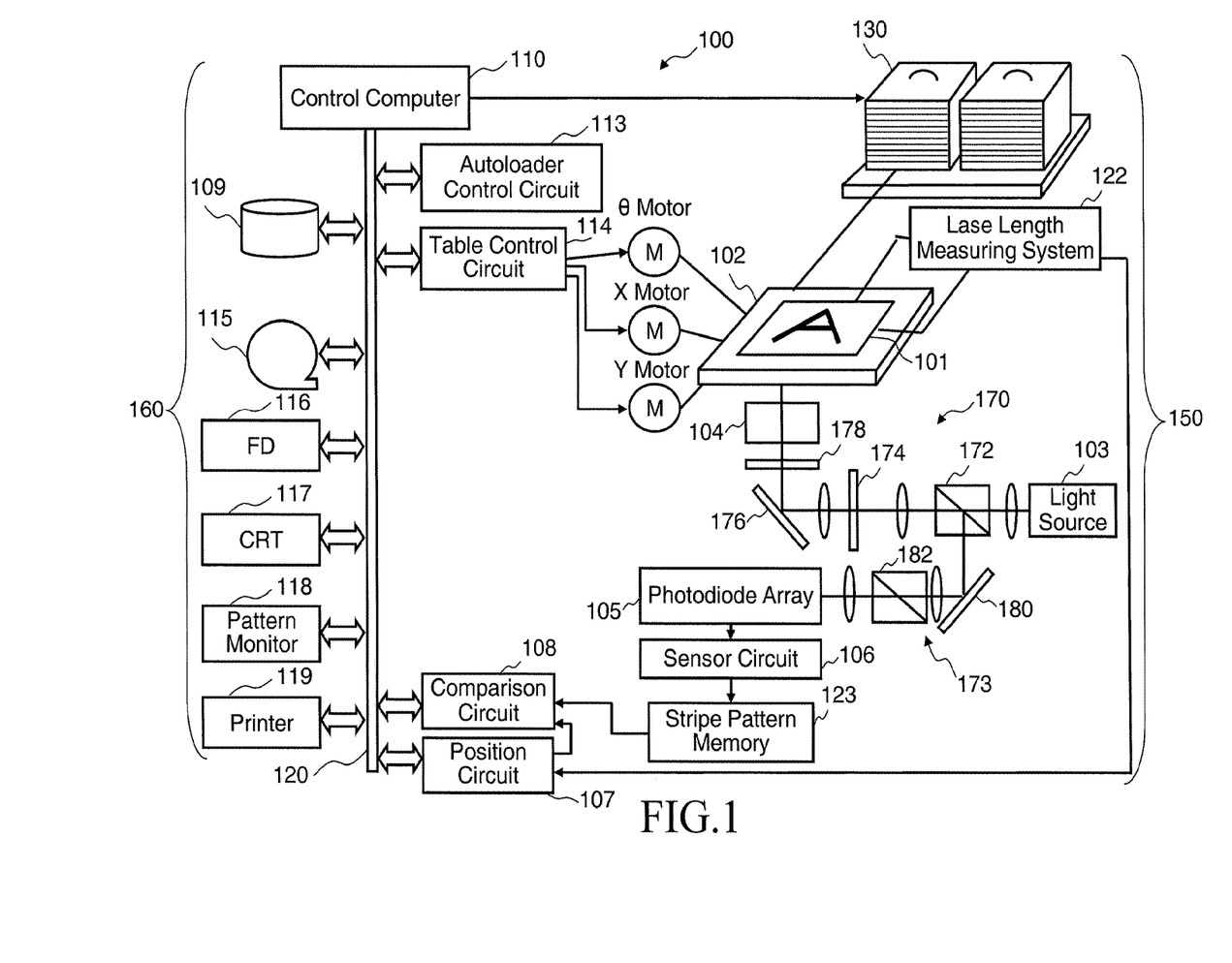
FIG. 1 illustrates a configuration of a pattern inspection apparatus according to a first embodiment.

FIG. 1 illustrates a configuration of a pattern inspection apparatus according to the first embodiment. As shown in FIG. 1, an inspection apparatus 100 that inspects defects of a pattern formed on a substrate 101 (example of inspection substrate) includes an optical image acquisition mechanism 150 and a control system circuit 160 (control circuit).

The optical image acquisition mechanism 150 includes a light source 103, a reflection illumination optical system 170 composed of one or more lenses, a polarization beam splitter 172, a half-wave plate (or "half-wave retarder") 174, a mirror 176, a half-wave plate 178, an objective lens 104, an XYθ table 102 arranged movably, an image forming optical system 173 composed of one or more lenses, a mirror 180, a polarization beam splitter 182, a sensor 105, a sensor circuit 106, a stripe pattern memory 123, and a laser length measuring system 122. On the XYθ table 102, there is placed the substrate 101 (example of inspection substrate) transmitted from a cassette 300. The substrate 101 is, for example, a template used for nanoimprint for transferring a pattern onto a wafer being a semiconductor substrate. On this template, there is formed a repetitive pattern having a size smaller than the resolution limit of light emitted from the light source 103. For example, a line and space pattern is formed as a repetitive pattern. Alternatively, for example, a hole pattern is formed. The substrate 101, for example, with its pattern forming surface facing downward is arranged on the XYθ table 102. It is preferable to use, as the sensor 105, for example, a line sensor or a two-dimensional sensor in which a photodiode array is mounted. Desirably, it is more preferable to use a TDI (Time Delay Integration) sensor.

In the control system circuit 160, a control computer 110 is connected, through a bus 120, to a position circuit 107, a comparison circuit 108, an autoloader control circuit 113, a table control circuit 114, a magnetic disk device 109, a magnetic tape device 115, a flexible disk device (FD) 116, a CRT 117, a pattern monitor 118, and a printer 119. The sensor circuit 106 is connected to the stripe pattern memory 123 which is connected to the comparison circuit 108. The XYθ table 102 is driven by the motors of the X-axis, Y-axis, and θ-axis.

In the inspection apparatus 100, an inspection optical system with large magnification is composed of the light source 103, the reflection illumination optical system 170, the polarization beam splitter 172, the half-wave plate 174, the mirror 176, the half-wave plate 178, the objective lens 104, the image forming optical system 173, the mirror 180, the polarization beam splitter 182, the sensor 105, and the sensor circuit 106. For example, an inspection optical system with magnification of 200 to 300 times is configured.

The XYθ table 102 is driven by the table control circuit 114 under the control of the control computer 110. The XYθ table 102 can be moved by a drive system such as a three-axis (X, Y, and θ) motor, which drives the table in the directions of x, y, and θ. For example, a linear motor can be used as each of these X, Y, and θ motors. The XYθ table 102 is movable in the horizontal direction and the rotation direction by the motors of the X-, Y-, and θ-axis. The XYθ table 102 is adjusted to the focus position (optical axis direction: Z axis direction) where an image of the pattern forming surface of the substrate 101 is focused on the sensor 105 under the control of the control computer 110. The movement position of the substrate 101 placed on the XYθ table 102 is measured by the laser length measuring system 122, and supplied to the position circuit 107.

FIG. 1 shows structure elements necessary for describing the first embodiment. It should be understood that other structure elements generally necessary for the inspection apparatus 100 may also be included therein.

Figure 2A:
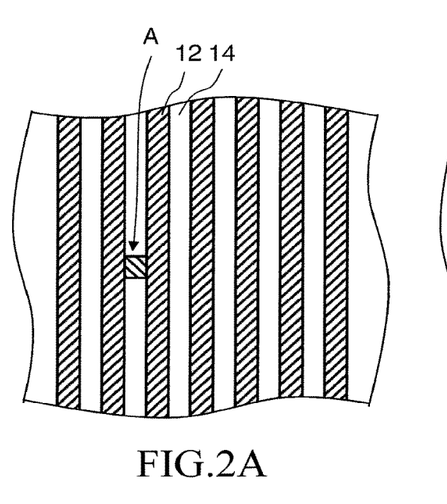
FIGS. 2A to 2C show examples of a repetitive pattern formed on an inspection substrate according to the first embodiment.
Figure 2B:
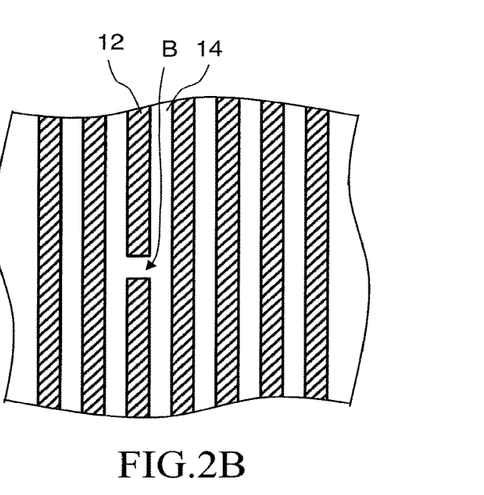
Figure 2C:
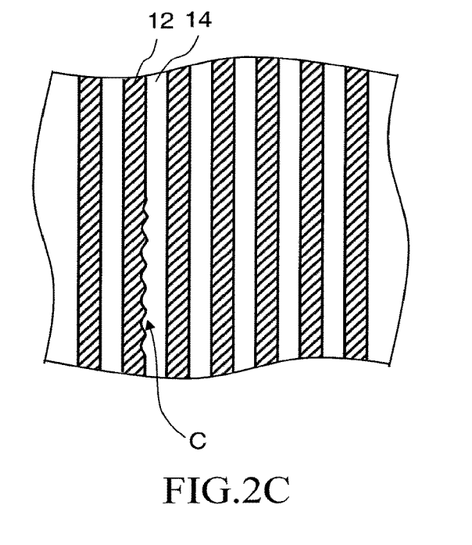

FIGS. 2A to 2C show examples of a repetitive pattern formed on an inspection substrate according to the first embodiment. As shown in FIGS. 2A to 2C, a line and space pattern in which a line pattern 12 and a space pattern 14 are alternately repeated with a periodicity is formed on the substrate 101. With the recent pattern miniaturization, the line pattern 12 and the space pattern 14 are alternately repeated by a line width size of 50 nm or less, for example. With respect to patterns formed on the substrate 101, a defect occurs, such as a short defect (A) due to shorting between connected line patterns 12 as shown in FIG. 2A, and an open defect (B) due to breaking in the line pattern 12 as shown in FIG. 2B. In addition, as shown in FIG. 2C, a dimensional disorder (edge roughness) (C) occurs at the edge part of the line pattern 12 (the space pattern 14). Since the short defect (A) and the open defect (B) lead to failure of a semiconductor circuit, they should be detected by the inspection apparatus 100. Regarding the light source 103, a laser beam (e.g., DUV light) (example of ultraviolet light) with a wavelength of about 190 to 200 nm, for example, is emitted as an inspection illumination light therefrom. However, a repetitive pattern smaller than the resolution limit of ultraviolet light is formed on the substrate 101. Accordingly, even if the repetitive pattern smaller than the resolution limit is irradiated with an illumination light for inspection so that the sensor 105 can capture its transmission image or reflection image, since the image acquired is blurred, it is difficult to identify the shapes of the line pattern 12 and the space pattern 14.

Then, according to the first embodiment, a defective portion is specified by utilizing the phenomena that if there is a defect in a repetitive pattern with a periodic regularity, disturbance (disorder) occurs in the periodicity, and that if a defective portion where periodicity disturbance occurs is image-captured, disturbance (disorder) occurs in the polarization state of light of the pattern image. Furthermore, since a dimension error of the short defect (A) or the open defect (B) is larger than that of the edge roughness (C), periodicity disturbance appears larger than that of the edge roughness (C). Therefore, by utilizing such difference, it is possible to distinguish the short defect (A) and the open defect (B) resulting in failure of an electronic circuit from the edge roughness (C) not resulting in failure of an electronic circuit.

Figure 3:
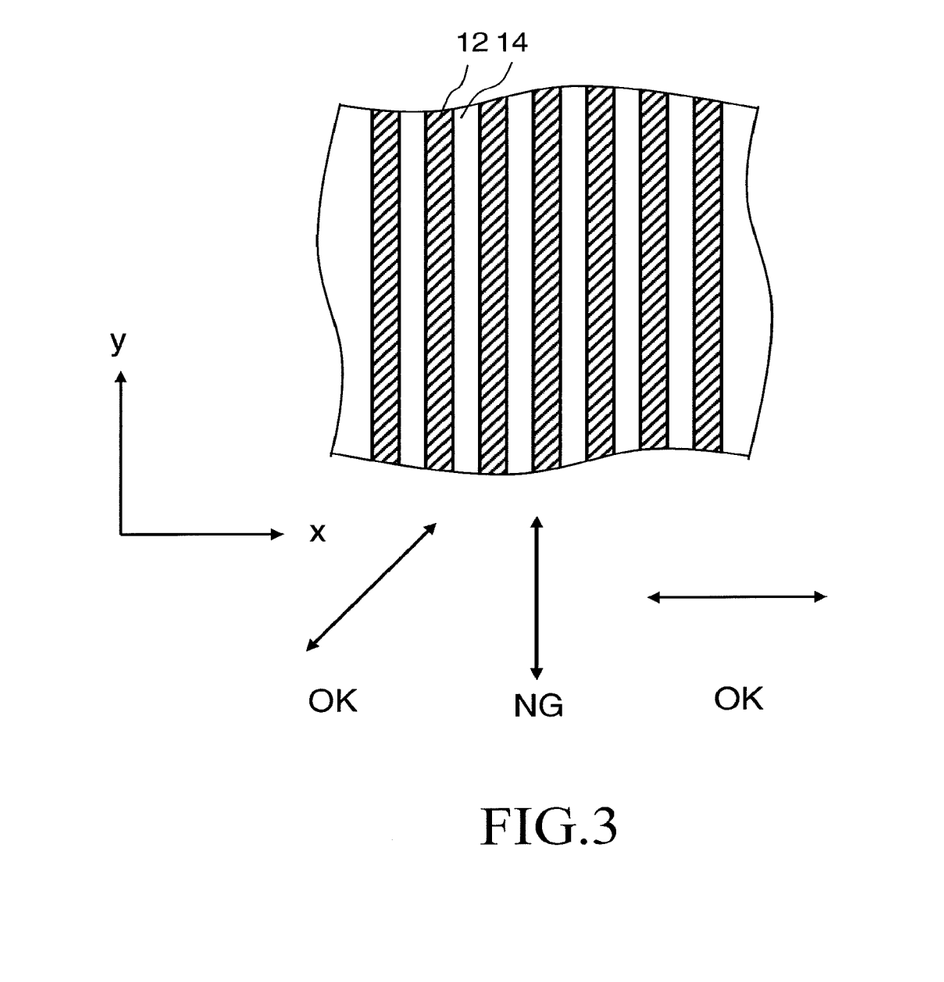
FIG. 3 shows an example of a relation between a repetitive pattern and a polarization state of an illumination light according to the first embodiment.

FIG. 3 shows an example of a relation between a repetitive pattern and a polarization state of an illumination light according to the first embodiment. Here, the case of a linearly polarized illumination light is described. If a repetitive pattern is irradiated with a linearly polarized light with a polarization direction parallel to the longitudinal direction of the line pattern 12, for example, of the repetitive pattern, disturbance does not occur or is unlikely to occur in the polarization state of light of an acquired pattern image. Therefore, the linearly polarized light with a polarization direction being the same as the longitudinal direction (y direction in FIG. 3) of the line pattern 12, for example, of the repetitive pattern cannot be used (NG) as an illumination light. By contrast, if a repetitive pattern is irradiated with a linearly polarized light with a polarization direction (x direction in FIG. 3) orthogonal to the longitudinal direction of the line pattern 12, for example, of the repetitive pattern, disturbance of the polarization state can be measured. However, it is difficult for the inspection apparatus 100 to identify in which direction the longitudinal direction (direction orthogonal to repeating direction) of the line pattern 12, for example, of the repetitive pattern faces on the inspection substrate 101. Therefore, for example, even if the linearly polarized light with a polarization direction in the x direction shown in FIG. 3 is used as the illumination light, if the direction of the repetitive pattern formed on the substrate 101 differs from the direction in FIG. 3 by 90°, it becomes difficult to measure disturbance of the polarization state. Accordingly, there is a risk in using the linearly polarized light with a polarization direction in the x direction as the illumination light. Usually, however, the direction of the repetitive pattern formed on the substrates 101 such as a template is parallel or orthogonal to the x, or y direction which has been set previously for the substrate 101. Therefore, if the repetitive pattern is irradiated with a linearly polarized light with a polarization direction not in the x or y direction which has been set previously for the substrate 101, but, for example, in the 45° direction (45° direction from the x axis in FIG. 3), disturbance of the polarization state can be measured irrespective of the direction of the repetitive pattern formed on the substrate 101.

Figure 4:
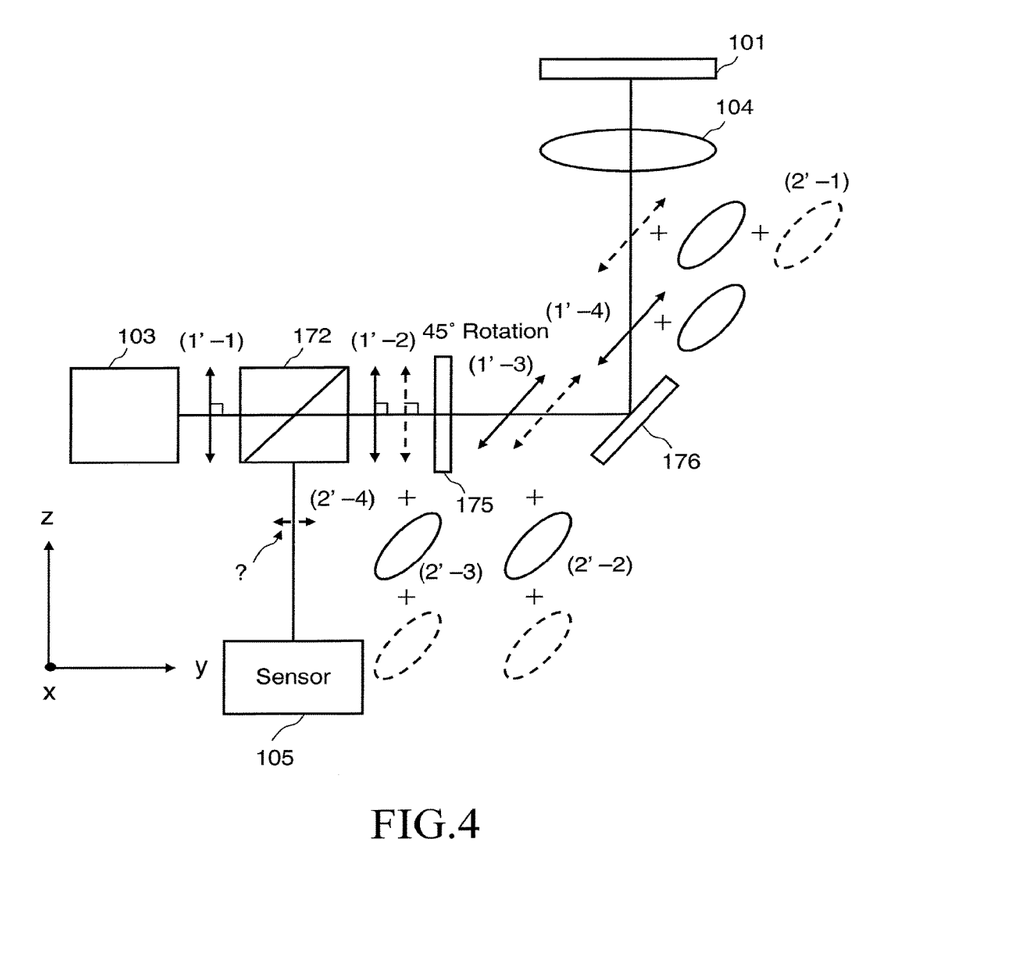
FIG. 4 shows an example of a polarization state on an optical path according to a comparative example to the first embodiment.

FIG. 4 shows an example of a polarization state on an optical path according to a comparative example to the first embodiment. In FIG. 4, lenses other than the objective lens 104 are not shown. FIG. 4 shows the case in which the substrate 101 is arranged to be parallel with the x-y plane configured by x and y axes in the x, y, and z axes mutually orthogonal, and in which the repetitive pattern is repeated in the y direction (90° from the x axis in the x-y plane) (in the case of the longitudinal direction of the line pattern 12 being in the x direction (0° from the x axis in the x-y plane). The light source 103 emits a linearly polarized ultraviolet light (e.g., P wave) (1'-1) which travels in the y direction and whose polarization direction (electric field oscillation direction) is the z direction (90° from the x axis in the x-z plane). This ultraviolet light (1'-1) enters the polarization beam splitter 172. The polarization beam splitter 172 makes the light (e.g., P wave) which travels in the y direction and whose polarization direction (electric field oscillation direction) is the z direction (90° from the x axis in the x-z plane) pass therethrough. Therefore, while maintaining the polarization state, the linearly polarized ultraviolet light (1'-1) passes through the polarization beam splitter 172. The linearly polarized ultraviolet light (1'-2) having passed through the polarization beam splitter 172 enters the half-wave plate 175 whose angle of the crystal axis (or "optical axis of half-wave plate") is set at −22.5° with respect to the x axis in the x-z plane. The half-wave plate 175 whose angle of the crystal axis is set at −22.5° rotates by −45° the polarization direction (electric field oscillation direction) of the light (e.g., P wave) which travels in the y direction and whose polarization direction is the z direction (90° from the x axis in the x-z plane). Therefore, in this case, the linearly polarized ultraviolet light (1'-2) with a polarization direction rotated by −45° (45° from the x axis in the x-z plane) passes through the half-wave plate 175. Thereby, the ultraviolet light (1'-3) having passed through the half-wave plate 175 is a linearly polarized light which travels in the y direction and whose polarization direction is 45° with respect to the x axis in the x-z plane. The linearly polarized ultraviolet light (1'-3) is reflected in the z direction by the mirror 176. Then, the ultraviolet light (1'-4) reflected by the mirror 176 is focused by the objective lens 104 so as to irradiate the surface of the substrate 101, as an illumination light. Ideally, the ultraviolet light (1'-4) should become a linearly polarized ultraviolet light which travels in the z direction and whose polarization direction (electric field oscillation direction) is 45° from the x axis in the x-y plane, and irradiate the repetitive pattern. Thereby, disturbance of a polarization state due to a pattern defect is to be measured irrespective of the direction of the repetitive pattern formed on the substrate 101. However, when the linearly polarized ultraviolet light (1'-3) as described above is reflected by the mirror 176, disturbance occurs in the polarization state of the reflected ultraviolet light (1'-4) in many cases.

Figure 5A:
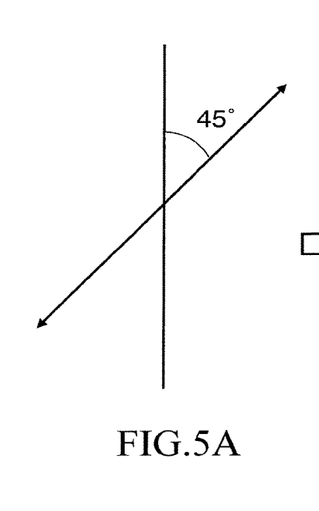
FIGS. 5A and 5B show an example of a polarization state of light reflected by a mirror according to the first embodiment.
Figure 5B:
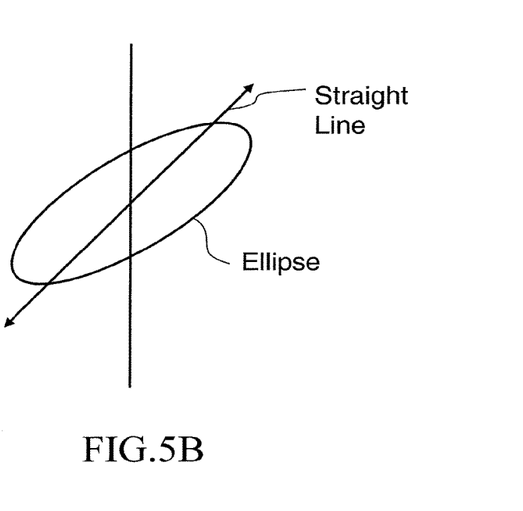

FIGS. 5A and 5B show an example of a polarization state of light reflected by a mirror according to the first embodiment. As shown in FIG. 5A, if a linearly polarized light with a polarization direction at 45° is orthogonally reflected by the mirror 176, disturbance occurs in the polarization state of the linearly polarized light with a polarization direction at 45°. For example, as shown in FIG. 5B, it becomes the polarization state where the linearly polarized light with a polarization direction at 45° and polarization disturbance components such as elliptical polarization are combined. Although an unpolarized mirror can be made technically, since a huge cost will be incurred, it is not realistic. Therefore, the polarization state of the ultraviolet light (1'-4) after being reflected by the mirror 176 shown in FIG. 4 is a polarization state where the linearly polarized light with a polarization direction at 45° and polarization disturbance components such as elliptical polarization are combined, for example. If a repetitive pattern being smaller than the resolution limit and having a periodic regularity is irradiated with the ultraviolet light (1'-4) in the polarization state where the linear polarization at 45° has been disturbed, disturbance (dotted line) of the polarization state, resulting from a pattern defect, is further added to the ultraviolet light (2'-1) reflected from the substrate 101. In the return path from the substrate 101, the polarization state of the ultraviolet light (2'-2) after reflection will further be disturbed because the ultraviolet light (2'-1) is reflected by the mirror 176.

Next, in the return path, the ultraviolet light (2'-2) enters the half-wave plate 175. Therefore, here, the ultraviolet light (2-2) passes through the half-wave plate 175, with a polarization direction rotated by 45° (90° from the x axis in the x-z plane). Thereby, the ultraviolet light (2-3) having passed through the half-wave plate 175 is an ultraviolet light traveling in the y direction and having a polarization state where a component of a linearly polarized light at 90° with respect to the x axis in the x-z plane, and polarization disturbance components such as elliptical polarization, etc. are combined.

Further, in the return path, the ultraviolet light (2'-3) enters the polarization beam splitter 172. In the ultraviolet lights (2'-3), the component of a linearly polarized light at 90° with respect to the x axis in the x-z plane passes through the polarization beam splitter 172. On the other hand, with respect to, for example, an elliptical polarization component being a polarization state disturbance, a part (component of a linearly polarized light at 0° with respect to x axis in x-z plane: S wave component) of the component is reflected by the polarization beam splitter 172. The ultraviolet light (2'-4) of the linearly polarized light component to be at 0° with respect to the x axis in the x-z plane, reflected by the polarization beam splitter 172, enters the sensor 105. Thereby, the sensor 105 can capture an image composed of components including a polarization state disturbance.

However, the image captured by the sensor 105 in the structure of the comparative example is just an image resulting from a polarization state where polarization state disorder caused by the mirror 176 in the forward path, polarization state disorder occurred in the substrate 101, and polarization state disorder caused by the mirror 176 in the return path are mixed. Therefore, it is difficult to determine whether an acquired pattern image is resulting from polarization state disorder caused by a mirror or resulting from polarization state disorder caused by a pattern defect.

By contrast, according to the first embodiment, it is structured such that the mirror 176 does not generate disturbance in the polarization state of an illumination light, in the forward path.

Figure 6:
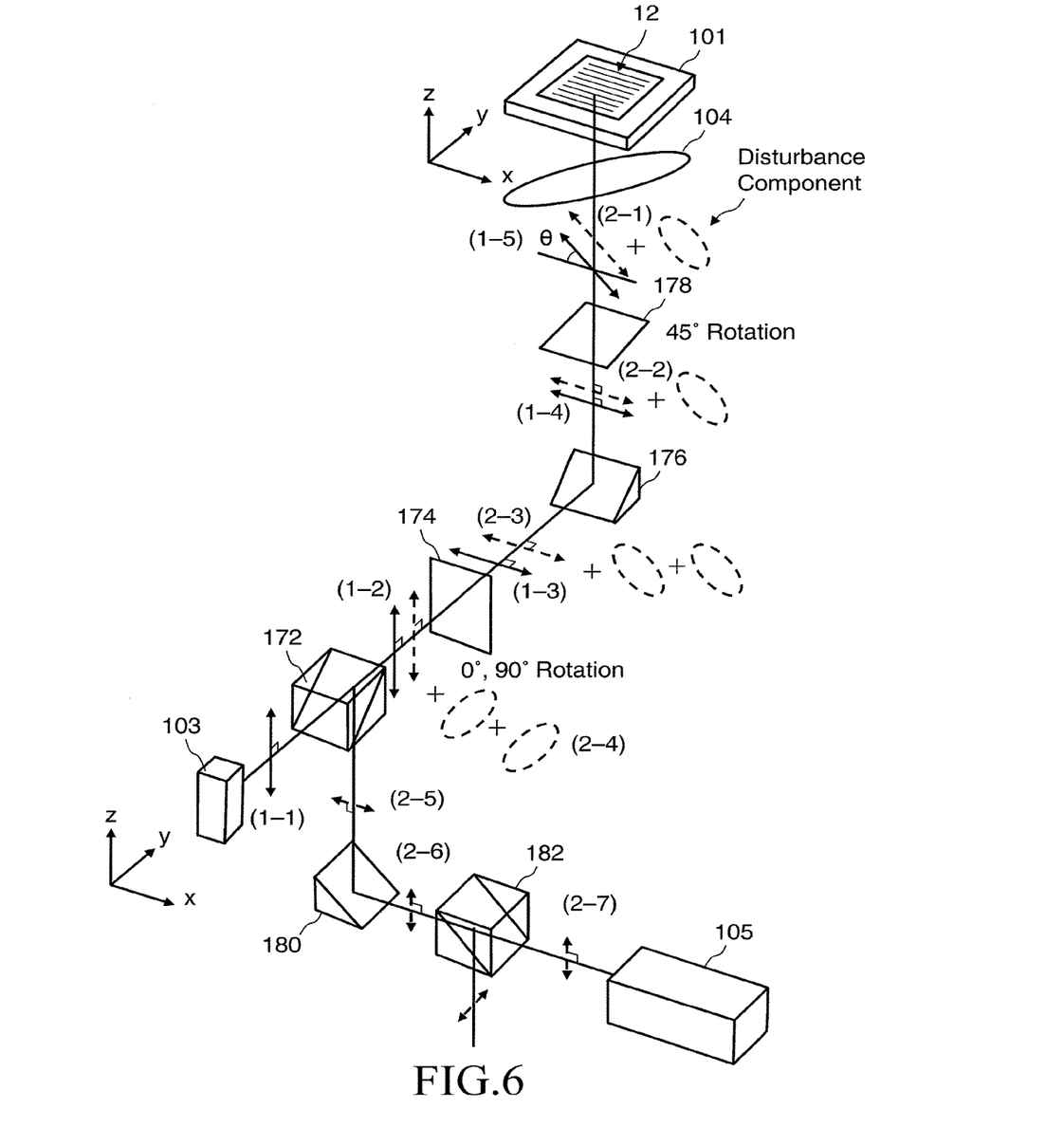
FIG. 6 shows an example of a polarization state in an optical path according to the first embodiment.

FIG. 6 shows an example of a polarization state in an optical path according to the first embodiment. In FIG. 6, lenses other than the objective lens 104 are not shown. In FIG. 6, the substrate 101 on which there is formed a repetitive pattern having a size smaller than the resolution limit of the ultraviolet light concerned used as an inspection light is arranged on the XYθ table table 102 (stage) such that the substrate 101 is parallel with the x-y plane configured by x and y axes in the x, y, and z axes mutually orthogonal, and the repetitive pattern is repeated in the direction parallel or orthogonal to the x direction (0° from the x axis in the x-y plane) (third electric field oscillation direction). FIG. 6 shows the case where the substrate 101 is arranged to be parallel with the x-y plane configured by x and y axes in the x, y, and z axes mutually orthogonal, and the repetitive pattern is repeated in the y direction (90° from the x axis in the x-y plane) (in the case of the longitudinal direction of the line pattern 12 being in the x direction (0° from the x axis in the x-y plane).

The light source 103 emits a linearly polarized ultraviolet light (e.g., P wave) (1-1) which travels in the y direction and whose polarization direction (electric field oscillation direction) is the z direction (90° from the x axis in the x-z plane). The polarization state of this ultraviolet light (1-1) may be adjusted using a polarization element (not shown) after being emitted from the light source 103.

This ultraviolet light (1-1) enters the polarization beam splitter 172 arranged in the optical path between the light source 103 and the half-wave plate 174 (first half-wave plate). The polarization beam splitter 172 makes the light (e.g., P wave) which travels in the y direction and whose polarization direction (electric field oscillation direction) is the z direction (90° from the x axis in the x-z plane) pass therethrough. Therefore, while maintaining the polarization state, the linearly polarized ultraviolet light (1-1) passes through the polarization beam splitter 172.

In the forward path, the linearly polarized ultraviolet light (1-2) having passed through the polarization beam splitter 172 enters the half-wave plate 174 whose angle of the crystal axis is set at, for example, 0 or 45° with respect to the x axis in the x-z plane. The half-wave plate 174 (first half-wave plate) receives the linearly polarized ultraviolet light (1-2) traveling in the y direction and having a polarization direction (first electric field oscillation direction) in the z direction (90° from the axis in the x-z plane), and outputs a linearly polarized light whose polarization direction (second electric field oscillation direction) is obtained by rotating the polarization direction (first electric field oscillation direction) of the ultraviolet light (1-2) by an integer multiple of 90°. For example, the half-wave plate 174, whose angle of the crystal axis is set at 45°, rotates by 90° the polarization direction (electric field oscillation direction) of a light (e.g., P wave) traveling in the y direction and having a polarization direction in the z direction (90° from the x axis in the x-z plane). Therefore, in this case, the linearly polarized ultraviolet light (1-2) with a polarization direction rotated by 90° (0 or 180° from the x axis in the x-z plane) passes through the half-wave plate 174. Thereby, the ultraviolet light (1-3) having passed through the half-wave plate 174 is a linearly polarized light which travels in the y direction and whose polarization direction is 0° with respect to the x axis in the x-z plane.

For example, the half-wave plate 174, whose angle of the crystal axis is set at 0°, rotates by 0° the polarization direction (electric field oscillation direction) of a light (e.g., P wave) traveling in the y direction and having a polarization direction in the z direction (90° from the x axis in the x-z plane). In other words, the polarization direction is maintained. Therefore, in this case, the linearly polarized ultraviolet light (1-2) with a maintained polarization direction state (90° from the x axis in the x-z plane) passes through the half-wave plate 174. Thereby, the ultraviolet light (1-3) having passed through the half-wave plate 174 is a linearly polarized light which travels in the y direction and whose polarization direction is 90° with respect to the x axis in the x-z plane. Note that, hereafter, description is continued on the assumption that the polarization direction is rotated by 90° by the half-wave plate 174.

The linearly polarized ultraviolet light (1-3) is reflected in the z direction by the mirror 176. The mirror 176 reflects the linearly polarized light traveling in the y direction and having a polarization direction (example of second electric field oscillation direction) at 0° with respect to the x axis in the x-z plane, and outputs a linearly polarized light with a polarization direction (third electric field oscillation direction) parallel or orthogonal to the polarization direction (example of second electric field oscillation direction) at 0° with respect to the x axis in the x-z plane. For example, the linearly polarized ultraviolet light (1-3) traveling in the y direction and having a polarization direction (second electric field oscillation direction) in the x direction (0° from the x axis in the x-z plane) enters the mirror 176 which performs reflection in the z direction. Here, by making the linearly polarized ultraviolet light (1-3) traveling in the y direction and having a polarization direction (second electric field oscillation direction) in the x direction (0° from the x axis in the x-z plane) enter the mirror 176 which performs reflection in the z direction, it becomes possible to avoid generating polarization state disturbance in the reflected linearly polarized ultraviolet light (1-4). In the case of performing reflection in the z direction, since it reflects axial-symmetrically, the reflected linearly polarized ultraviolet light (1-4) is a linearly polarized light traveling in the z direction and having a polarization direction (third electric field oscillation direction) at 0° from the x axis in the x-y plane. Therefore, no phase difference occurs before and after the light incidence, and no polarization state disturbance occurs in the reflected linearly polarized ultraviolet light (1-4). Thereby, according to the first embodiment, it is possible to suppress polarization state disturbance caused by the mirror 176 in the forward path. As described above, in the case of reflecting a linearly polarized ultraviolet light by the mirror 176, the linearly polarized ultraviolet light (1-3) is controlled to be in the electric field oscillation direction where the electric field oscillation direction of the incident light to the mirror 176, and the electric field oscillation direction of the reflected light from the mirror 176 are parallel. Then, the controlled linearly polarized ultraviolet light (1-3) is reflected by the mirror 176. This effect can also be similarly acquired in the case of incidence of the linearly polarized ultraviolet light (1-3) traveling in the y direction and having a polarization direction (another example of second electric field oscillation direction) in the z direction (90° from the x axis in the x-z plane). In such a case, the reflected linearly polarized ultraviolet light (1-4) is a linearly polarized light traveling in the z direction and having a polarization direction (another example of third electric field oscillation direction) at 90° from the x axis in the x-y plane. In such a case, when reflecting the linearly polarized ultraviolet light (1-3) by the mirror 176, the linearly polarized ultraviolet light (1-3) is controlled to be in the electric field oscillation direction where the electric field oscillation direction of the incident light to the mirror 176, and the travel direction of the reflected light from the mirror 176 are parallel.

However, when the linearly polarized ultraviolet light (1-3) traveling in the y direction and having a polarization direction (second electric field oscillation direction) in the x direction (0° from the x axis in the x-z plane) enters the mirror 176 which performs reflection in the z direction, the reflected linearly polarized ultraviolet light (1-4) is a linearly polarized light traveling in the z direction and having a polarization direction (third electric field oscillation direction) at 0° from the x axis in the x-y plane. Therefore, if the linearly polarized light remains as it is, it becomes perpendicular (or parallel to longitudinal direction (x direction) of the line pattern 12) to the repeating direction (y direction) of the repetitive pattern. Then, according to the first embodiment, the polarization direction is shifted using the half-wave plate 178. In other words, the electric field oscillation direction of the reflected light from the mirror 176 is controlled to be an angle different from an integer multiple of 90° relative to the periodic direction of the repetitive pattern formed on the substrate repeating by the size smaller than the resolution limit of the ultraviolet light. Also, in the case of using the linearly polarized ultraviolet light (1-4) which travels in the z direction and whose polarization direction (another example of third electric field oscillation direction) is 90° from the x axis in the x-y plane, it is similarly controlled to be an angle different from an integer multiple of 90° relative to the periodic direction of the repetitive pattern.

In the forward path, the linearly polarized ultraviolet light (1-4) reflected by the mirror 176 enters the half-wave plate 178 whose angle of the crystal axis is set at, for example, 22.5° with respect to the x axis in the x-y plane. The half-wave plate 178 (second half-wave plate) converts a reflected linearly polarized light, which travels in the z direction and whose polarization direction (third electric field oscillation direction) is 0° from the x axis in the x-y plane, into a linearly polarized ultraviolet light (1-5) whose polarization direction (fourth electric field oscillation direction) is rotated by an angle different from an integer multiple of 90°, and outputs the linearly polarized ultraviolet light (1-5). For example, if the angle of the crystal axis is 22.5°, the polarization direction at 0° from the x axis in the x-y plane can be rotated to the polarization direction at 45° from the x axis in the x-y plane.

In the forward path, the ultraviolet light (1-5) having passed through the half-wave plate 178 enters the objective lens 104. The objective lens 104 makes the linearly polarized ultraviolet light (1-5) with a polarization direction (fourth electric field oscillation direction) rotated to be 45° from the x axis in the x-y plane by the half-wave plate 178 illuminate the repetitive pattern formed on the substrate 101. Specifically, the objective lens 104 focuses, as an illumination light, the ultraviolet light (1-5) having passed through the half-wave plate 178 onto the surface of the substrate 101 to be irradiated. Thereby, the ultraviolet light (1-5), as a linearly polarized ultraviolet light traveling in the z direction and having a polarization direction (fourth electric field oscillation direction) at 45° from the x axis in the x-y plane, can irradiate a repetitive pattern. Therefore, disturbance of the polarization state caused by a pattern defect can be measured from the reflected image irrespective of the direction of the repetitive pattern formed on the substrate 101.

As described above, by rotating the polarization direction of the ultraviolet light (1-4) by the half-wave plate 178, the polarization direction can be a shifted angle different from a direction parallel or orthogonal to the repeating direction (direction orthogonal to longitudinal direction of the line pattern 12) of a repetitive pattern.

Although 45° is desirable as the angle for rotating the polarization direction of the ultraviolet light (1-4) by the half-wave plate 178, it is not limited thereto. It is sufficient to perform rotation to be an angle out of ranges of from −5° to 5°, from 85° to 95°, from 175° to 185°, and from 265° to 275° from the x axis in the x-y plane. Thereby, 10% of an amplitude in an electric field oscillation direction can be excluded, and therefore, polarization state disturbance components caused by a repetitive pattern can certainly be detected.

By the structure as described above, according to the first embodiment, a repetitive pattern can be irradiated with the linearly polarized ultraviolet light (1-5) not including polarization state disorder resulting from the mirror 176. Therefore, if polarization state disorder is included in an acquired reflected light, it can be determined that this disorder results from a pattern defect. Further, if a repetitive pattern does not include a defect, no polarization state disorder is included in an acquired reflected light. Thus, if polarization state disorder is not included in the acquired reflected light, it can be determined that a repetitive pattern does not include a defect.

In the return path, a reflected light from a repetitive pattern smaller than the resolution limit is received by the sensor 105, through, in order, the half-wave plate 178, the mirror 176, the half-wave plate 174, and the polarization beam splitter 172. It will be sequentially described below.

In the return path from the substrate 101, the ultraviolet light (2-1) being a reflected light from a repetitive pattern enters the half-wave plate 178 through the objective lens 104. If a repetitive pattern does not include a pattern defect, the ultraviolet light (2-1) is in the polarization state of a linearly polarized light traveling in the −z direction and having a polarization direction (fourth electric field oscillation direction) at 45° from the x axis in the x-y plane. If a repetitive pattern includes a pattern defect (or edge roughness), the ultraviolet light (2-1) is in the polarization state where a linearly polarized light component for traveling in the −z direction and having a polarization direction (fourth electric field oscillation direction) at 45° from the x axis in the x-y plane, and polarization disturbance components such as elliptical polarization are mixed. If a repetitive pattern does not include a pattern defect (and edge roughness), the half-wave plate 178 rotates the polarization direction of the linearly polarized ultraviolet light (2-1) traveling in the −z direction and having a polarization direction (fourth electric field oscillation direction) at 45° from the x axis in the x-y plane in order to output a linearly polarized ultraviolet light (2-2) with a polarization direction at 0° from the x axis. If a repetitive pattern includes a pattern defect (or edge roughness), the half-wave plate 178 rotates the polarization direction of the ultraviolet light (2-1) in the polarization state, where a linearly polarized light component for traveling in the −z direction and having a polarization direction (fourth electric field oscillation direction) at 45° from the x axis in the x-y plane, and polarization disturbance components such as elliptical polarization are mixed, in order to output the ultraviolet light (2-2) in the polarization state where a linearly polarized light component of a polarization direction at 0° from the x axis and polarization disturbance components such as elliptical polarization are mixed.

In the return path, the ultraviolet light (2-2) enters the mirror 176. If a repetitive pattern does not include a pattern defect (and edge roughness), the mirror 176 reflects the linearly polarized ultraviolet light (2-2) traveling in the −z direction and having a polarization direction at 0° with respect to the x axis in the x-y plane so as to output a linearly polarized ultraviolet light (2-3) traveling in the −y direction and having a polarization direction at 0° with respect to the x axis in the x-z plane. Thus, if there is no pattern defect (and edge roughness), it is possible to perform reflection in the polarization state having no disturbance. Thereby, according to the first embodiment, polarization state disorder by the mirror 176 can be suppressed in the return path. This effect can also be similarly acquired in the case of incidence of the linearly polarized ultraviolet light (2-2) traveling in the −z direction and having a polarization direction at 90° with respect to the x axis in the x-y plane.

If a repetitive pattern includes a pattern defect (or edge roughness), the mirror 176 reflects the ultraviolet light (2-2) in the polarization state where a linearly polarized light component for traveling in the −z direction and having a polarization direction at 0° with respect to the x axis in the x-y plane, and an elliptical polarization component are mixed, and outputs the ultraviolet light (2-3) in the polarization state where a linearly polarized light component for traveling in the −y direction and having a polarization direction at 0° with respect to the x axis in the x-z plane, polarization disturbance components such as elliptical polarization resulting from a pattern defect, and polarization disturbance components such as elliptical polarization resulting from the mirror 176 are mixed.

Next, in the return path, the ultraviolet light (2-3) enters the half-wave plate 174. The polarization direction is rotated by 0 or 90° by the half-wave plate 174. In this case, since it was rotated by 90° in the forward path, it is also rotated by 90° in the return path. Therefore, if there is no pattern defect (and edge roughness), in this case, the ultraviolet light (2-4) having passed through the half-wave plate 174 is a linearly polarized ultraviolet light traveling in the −y direction, and having a polarization direction at 90° with respect to the x axis in x-z plane.

If a repetitive pattern includes a pattern defect (or edge roughness), the ultraviolet light (2-4) having passed through the half-wave plate 174 is an ultraviolet light in the polarization state where a linearly polarized light component for traveling in the −y direction and having a polarization direction at 90° with respect to the x axis in the x-z plane, polarization disturbance components such as elliptical polarization resulting from a pattern defect, and polarization disturbance components such as elliptical polarization resulting from the mirror 176 are mixed.

When the half-wave plate 174 makes a rotation by 0° (namely, when making no rotation) in the forward path, if there is no pattern defect (and edge roughness), since the ultraviolet light (2-3) is a linearly polarized ultraviolet light traveling in the −y direction and having a polarization direction at 90° with respect to the x axis in the x-z plane, the ultraviolet light (2-4) having passed through the half-wave plate 174 is a linearly polarized ultraviolet light traveling in the −y direction and having a polarization direction at 90° with respect to the x axis in the x-z plane. On the other hand, if there is a pattern defect (or edge roughness), since the ultraviolet light (2-3) is in the polarization state where a linearly polarized light component for traveling in the −y direction and having a polarization direction at 90° with respect to the x axis in the x-z plane, polarization disturbance components such as elliptical polarization resulting from a pattern defect, and polarization disturbance components such as elliptical polarization resulting from the mirror 176 are mixed, the ultraviolet light (2-4) having passed through the half-wave plate 174 is in the polarization state where a linearly polarized light component for traveling in the −y direction and having a polarization direction at 90° with respect to the x axis in the x-z plane, polarization disturbance components such as elliptical polarization resulting from a pattern defect, and polarization disturbance components such as elliptical polarization resulting from the mirror 176 are mixed.

Next, in the return path, the ultraviolet light (2-4) enters the polarization beam splitter 172. In the ultraviolet light (2-4), a linearly polarized light component to be at 90° with respect to the x axis in the x-z plane passes through the polarization beam splitter 172. Therefore, if there is no pattern defect (and edge roughness), all the ultraviolet light (2-4) passes through the polarization beam splitter 172. Therefore, the sensor 105 does not receive an image.

On the other hand, with respect to, for example, an elliptical polarization component being a polarization state disturbance, a part (component of a linearly polarized light at 0° with respect to x axis in x-z plane: S wave component) of the component is reflected by the polarization beam splitter 172. The ultraviolet light (2-5) of a linearly polarized light component to be at 0° with respect to the x axis in the x-z plane, reflected by the polarization beam splitter 172, results from the polarization disturbance just caused by a pattern defect (or edge roughness). Therefore, if the sensor 105 receives the ultraviolet light (2-5), when the intensity of the received light is greater than or equal to a threshold, it can be determined that the pattern defect has been generated at a position of measurement data which the received light has. When the intensity of the received light is less than the threshold, it can be determined that an edge roughness is generated at a position of measurement data which the received light has. However, in the first embodiment, the ultraviolet light (2-5) further passes through an optical element before reaching the sensor 105.

Next, in the return path, the ultraviolet light (2-5) of the linearly polarized light component to be at 0° with respect to the x axis in the x-z plane, reflected by the polarization beam splitter 172, enters the mirror 180. The mirror 180 reflects the linearly polarized ultraviolet light (2-5) which travels in the −z direction and whose polarization direction is 0° with respect to the x axis in the x-y plane, so as to output the linearly polarized ultraviolet light (2-6) which travels in the x direction and whose polarization direction is 90° with respect to the y axis in the y-z plane. Since it has only a linearly polarized light component of a polarization direction at 90° with respect to the y axis, polarization state disorder caused by the mirror 180 can be suppressed.

Next, in the return path, the ultraviolet light (2-6) reflected by the mirror 180 enters the polarization beam splitter 182 (example of analyzer). According to the first embodiment, as shown in FIGS. 1 and 6, the polarization beam splitter 182 (example of analyzer) is arranged in the optical path between the polarization beam splitter 172 and the sensor 105. Since the ultraviolet light (2-6) is a linearly polarized light traveling in the x direction and having a polarization direction at 90° with respect to the y axis in the y-z plane, it passes through the polarization beam splitter 182. If polarization disturbance occurs by the image forming optical system 173, etc. after being reflected by the polarization beam splitter 172, the polarization disturbance component can be eliminated by making the ultraviolet light (2-6) pass through the polarization beam splitter 182. With respect to polarization deviation occurred after being reflected by the polarization beam splitter 172, since its direction differs from that of polarization deviation occurred in the substrate 101, it is possible to separate it by the polarization beam splitter 182.

Next, in the return path, the linearly polarized ultraviolet light (2-7) having passed through the polarization beam splitter 182, which travels in the x direction and whose polarization direction is 90° with respect to the y axis in the y-z plane, is focused by the image forming optical system 173 so as to form an image on the surface of the sensor 105. Thus, the sensor 105 receives a reflected light from the repetitive pattern, smaller than the resolution limit, illuminated with a linearly polarized light with a polarization direction (fourth electric field oscillation direction) obtained by rotating the polarization direction (third electric field oscillation direction) of a light traveling in the z axis direction and having a polarization direction at 0° with respect to the x axis in the x-y plane by an angle different from an integer multiple of 90° by the half-wave plate 178 (second half-wave plate). Thereby, the ultraviolet light (2-7) resulting from polarization disturbance caused by a pattern defect (or edge roughness) is received by the sensor 105.

According to the first embodiment as described above, it is structured not to generate, in the forward path, polarization state disturbance of an illumination light caused by the mirror 176. Therefore, if a polarization disturbance component is included in a reflected light obtained in the return path, the position where a pattern defect (or edge roughness) is generated can be specified irrespective of polarization disturbance resulting from the mirror 176 of the return path.

Figure 7:
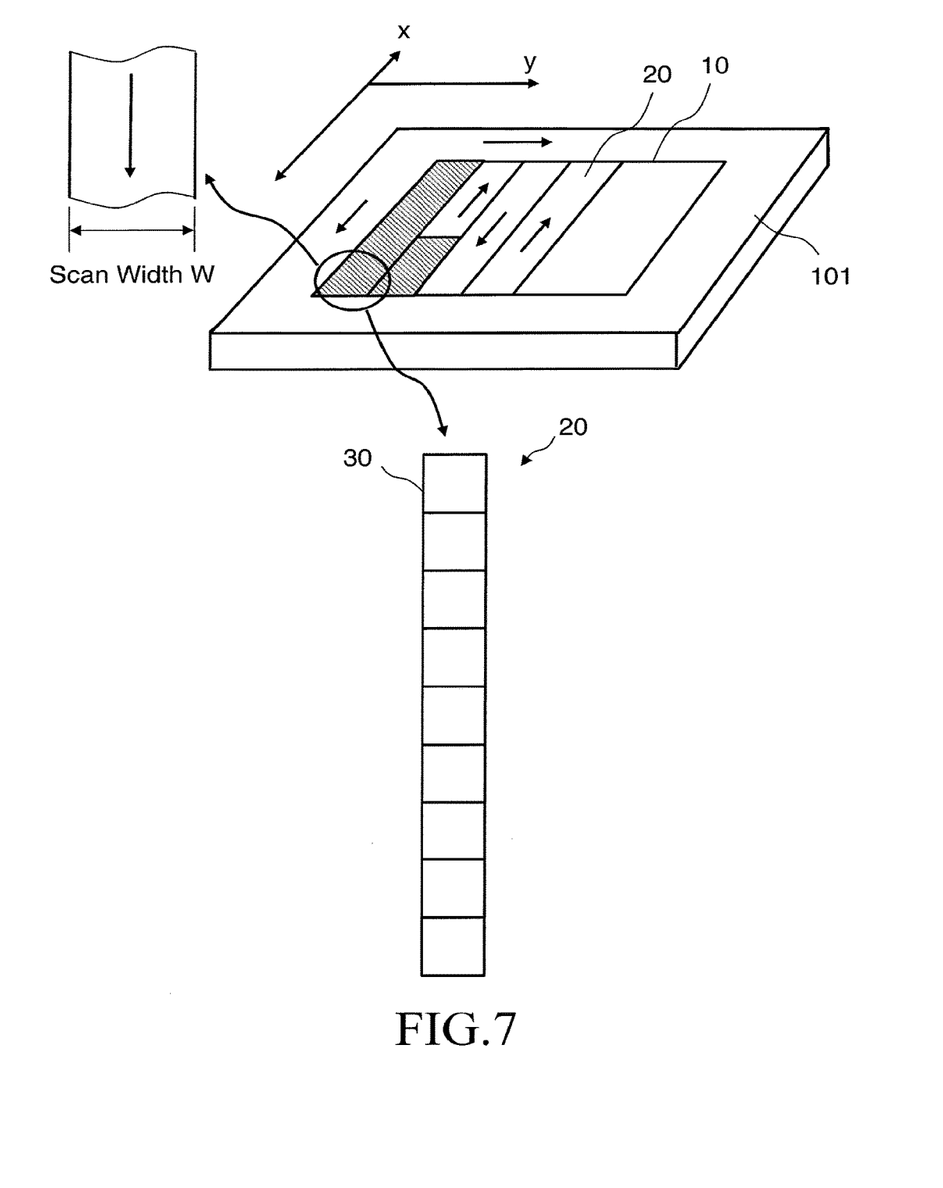
FIG. 7 is a conceptual diagram illustrating an inspection region according to the first embodiment.

FIG. 7 is a conceptual diagram illustrating an inspection region according to the first embodiment. As shown in FIG. 7, an inspection region 10 (entire inspection region) of the substrate 101 is virtually divided into a plurality of strip-shaped inspection stripes 20 each having a scan width W in the y direction, for example.

The inspection apparatus 100 acquires an image (stripe region image) from each inspection stripe 20. That is, with respect to each of the inspection stripes 20, the inspection apparatus 100 captures an image of a repetitive pattern arranged in the stripe region concerned by using the ultraviolet light (1-5) in the longitudinal direction (x direction) of the stripe region concerned. Then, the XYθ table 120 is moved in the x direction, and accordingly, the sensor 105, which continuously moves relatively in the x direction by the movement of the XYθ table 120, acquires an optical image. The sensor 105 continuously captures optical images each having a scan width W as shown in FIG. 7. After capturing an optical image in one inspection stripe 20, the sensor 105 moves in the y direction to the position of the next inspection stripe 20 and similarly captures another optical image having a scan width W continuously while moving in the direction reverse to the last image capturing direction. Thereby, the image capturing is repeated in the forward (FWD) and backward (BWD) directions, namely changing the direction reversely when advancing and returning.

The direction of the image capturing is not limited to repeating the forward (FWD) and backward (BWD) movement. Images may be captured in a fixed one direction. For example, it is sufficient to repeat FWD and FWD, or alternatively, to repeat BWD and BWD.

The pattern image focused/formed on the sensor 105 is photoelectrically converted by each light receiving element of the sensor 105, and further analog-to-digital (A/D) converted by the sensor circuit 106. Then, pixel data for an inspection stripe 20 to be measured is stored in the stripe pattern memory 123. When acquiring an optical image of the inspection stripe 20, the laser length measuring system 122 measures the position of the XYθ table 102. The measured position information is output to the position circuit 107. The position circuit 107 calculates the position of the substrate 101 by using the measured position information.

Then, the stripe region image is sent to the comparison circuit 108, with data indicating the position of the substrate 101 on the XYθ table 102 output from the position circuit 107. Measured target data (pixel data) is, for example, 8-bit unsigned data (256 gray scales), and indicates a gray level (light intensity) of brightness of each pixel.

The stripe region image input into the comparison circuit 108 is stored in the storage device (not shown). The comparison circuit 108 divides the stripe region image by a predetermined size (e.g., the same width as the scan width W) in the x direction such that the frame image of a target frame region 30 is clipped from the stripe region image (optical image) of the inspection stripe 20. For example, it is divided into frame images each having 512×512 pixels. By this processing, a plurality of frame images (optical images) corresponding to a plurality of frame regions 30 are acquired. The size of the frame region 30 does not necessarily need to be the same width as the scanning width W.

The comparison circuit 108 compares a gray scale value with a threshold, for each pixel, and determines whether there is a defect or not. If the gray scale value of the target pixel is greater than the threshold, it can be determined that the position of the pixel concerned is the position where a pattern defect occurs. If the gray scale value of the target pixel is not zero, but less than the threshold, it can be determined that it is the position where edge roughness (or measurement error) occurs. If the gray scale value of the target pixel is zero, it can be determined that it is a normal position where neither pattern defect nor edge roughness occurs.

Polarization disturbance resulting from edge roughness is smaller than polarization disturbance resulting from a pattern defect. Therefore, although the light received by the sensor 105 also includes a polarization disturbance component caused by the mirror 176 in the return path, even if a further polarization disturbance occurs by the mirror 176 in the return path in the polarization disturbance component resulting from edge roughness, it is still small as it is. Therefore, if the intensity of the light received by the sensor 105 is greater than or equal to the threshold, it can be determined irrespective of polarization disturbance caused by the mirror 176 in the return path that the position of the received light is the position where a pattern defect occurs.

Comparison results (determined results) are output to the magnetic disk device 109, magnetic tape device 115, flexible disk device (FD) 116, CRT 117, and pattern monitor 118, or output from the printer 119.

As described above, according to the first embodiment, it is possible to detect a pattern defect even when a repetitive pattern, being smaller than the resolution limit and having a periodic regularity, is irradiated using an illumination optical system where a mirror is arranged in the optical path.

In the above description, each " . . . circuit" includes a processing circuitry. As the processing circuitry, for example, an electric circuit, computer, processor, circuit board, quantum circuit, semiconductor device, or the like can be used. Each " . . . circuit" may use a common processing circuitry (same processing circuitry), or different processing circuitries (separate processing circuitries). In the case of using programs, the programs are stored in a recording medium, such as a magnetic disk device, magnetic tape device, FD, ROM (Read Only Memory), etc.

Embodiments have been explained referring to concrete examples described above. However, the present invention is not limited to these specific examples. In the above examples, a reflected light from a repetitive pattern smaller than a resolution limit is received, but it is not limited thereto. It is also preferable to receive a transmitted light of a repetitive pattern smaller than a resolution limit.

While the apparatus configuration, control method, and the like not directly necessary for explaining the present invention are not described, some or all of them can be selectively used on a case-by-case basis when needed. For example, although description of the configuration of the control circuit for controlling the inspection apparatus 100 is omitted, it should be understood that some or all of the configuration of the control circuit can be selected and used appropriately when necessary.

In addition, any other pattern inspection apparatus and pattern inspection method that include elements of the present invention and that can be appropriately modified by those skilled in the art are included within the scope of the present invention.

Additional advantages and modification will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A pattern inspection apparatus, comprising:
    a first half-wave plate configured to receive an ultraviolet light linearly polarized in a first electric field oscillation direction, and output a linearly polarized light polarized in a second electric field oscillation direction obtained by rotating the first electric field oscillation direction of the ultraviolet light by an integer multiple of 90°;
    a mirror configured to reflect the linearly polarized light polarized in the second electric field oscillation direction, and output a linearly polarized light polarized in a third electric field oscillation direction parallel or orthogonal to the second electric field oscillation direction;
    a second half-wave plate configured to convert the linearly polarized light polarized in the third electric field oscillation direction, which has been reflected, to a linearly polarized light polarized in a fourth electric field oscillation direction by rotating the linearly polarized light polarized in the third electric field oscillation direction by an angle different from an integer multiple of 90° so as to output the linearly polarized light polarized in the fourth electric field oscillation direction;
    a stage configured to mount thereon a substrate, on which a repetitive pattern having a size smaller than a resolution limit of the ultraviolet light is formed, such that the repetitive pattern is repeated in a direction parallel or orthogonal to the third electric field oscillation direction;
    an objective lens configured to make the linearly polarized light rotated in the fourth electric field oscillation direction by the second half-wave plate illuminate the repetitive pattern formed on the substrate, the linearly polarized light rotated in the fourth electric field oscillation direction illuminating the repetitive pattern formed on the substrate, being a linearly polarized light obtained through the ultraviolet light linearly polarized in the first electric field oscillation direction, the linearly polarized light polarized in the second electric field oscillation direction, and the linearly polarized light polarized in the third electric field oscillation direction in this order; and
    a sensor configured to receive a transmitted light of the repetitive pattern smaller than the resolution limit or a reflected light from the repetitive pattern smaller than the resolution limit, which has been irradiated with the linearly polarized light polarized in the fourth electric field oscillation direction obtained by rotating the third electric field oscillation direction by the angle different from the integer multiple of 90° by the second half-wave plate.

2. The apparatus according to claim 1, further comprising:
a light source configured to emit the ultraviolet light; and
a polarization beam splitter arranged in an optical path between the light source and the first half-wave plate.

3. The apparatus according to claim 2, wherein the reflected light from the repetitive pattern smaller than the resolution limit is received by the sensor, through, in order, the second half-wave plate, the mirror, the first half-wave plate, and the polarization beam splitter.

4. The apparatus according to claim 3, further comprising:
an analyzer arranged in an optical path between the polarization beam splitter and the sensor.

5. The apparatus according to claim 1, wherein the substrate includes a template for nanoimprinting.

6. The apparatus according to claim 1, wherein the second electric field oscillation direction is orthogonal to a travel direction of the linearly polarized light polarized in the second electric field oscillation direction.

7. The apparatus according to claim 6, wherein the mirror reflects, as the linearly polarized light polarized in the third electric field oscillation direction, the linearly polarized light polarized in the second electric field oscillation direction toward a direction orthogonal to the travel direction of the linearly polarized light polarized in the second electric field oscillation direction.

8. The apparatus according to claim 7, wherein the third electric field oscillation direction is orthogonal to a travel direction of the linearly polarized light polarized in the third electric field oscillation direction.

9. A pattern inspection method, comprising:
reflecting by a mirror an ultraviolet light linearly polarized which is controlled to be in a first electric field oscillation direction where the first electric field oscillation direction of an incident light into the mirror and a second electric field oscillation direction of a reflected light from the mirror are parallel to each other in a case of reflecting by the mirror the ultraviolet light linearly polarized;
controlling the second electric field oscillation direction of the reflected light to be a third electric field oscillation direction of an angle different from an integer multiple of 90° relative to a periodic direction of a repetitive pattern formed on a substrate repeating by a size smaller than a resolution limit of the ultraviolet light;
irradiating the substrate with the reflected light having been controlled to be the third electric field oscillation direction of the angle different from the integer multiple of 90° relative to the periodic direction of the repetitive pattern, the reflected light having been controlled to be the third electric field oscillation direction for irradiating the substrate, being a linearly polarized light obtained through the ultraviolet light linearly polarized controlled to be in the first electric field oscillation direction, and the reflected light polarized in the second electric field oscillation direction in this order;
receiving a pattern image of the repetitive pattern, reflected from the substrate, by a sensor through the mirror; and
inspecting the pattern image received by the sensor.

10. A pattern inspection method, comprising:
reflecting by a mirror an ultraviolet light linearly polarized which is controlled to be in a first electric field oscillation direction where the first electric field oscillation direction of an incident light into the mirror and a travel direction of a reflected light polarized in a second electric field oscillation direction from the mirror are parallel to each other in a case of reflecting by the mirror the ultraviolet light linearly polarized;
controlling the second electric field oscillation direction of the reflected light to be a third electric field oscillation direction of an angle different from an integer multiple of 90° relative to a periodic direction of a repetitive pattern formed on a substrate repeating by a size smaller than a resolution limit of the ultraviolet light;
irradiating the substrate with the reflected light having been controlled to be the third electric field oscillation direction of the angle different from the integer multiple of 90° relative to the periodic direction of the repetitive pattern, the reflected light having been controlled to be the third electric field oscillation direction for irradiating the substrate, being a linearly polarized light obtained through the ultraviolet light linearly polarized controlled to be in the first electric field oscillation direction, and the reflected light polarized in the second electric field oscillation direction in this order;
receiving a pattern image of the repetitive pattern, reflected from the substrate, by a sensor through the mirror; and
inspecting the pattern image received by the sensor.

* * * * *